(12) United States Patent
Song et al.

(10) Patent No.: US 10,309,882 B2
(45) Date of Patent: Jun. 4, 2019

(54) DROP BALL TEST FIXTURE

(71) Applicants: BOE TECHNOLOGY GROUP CO., LTD., Beijing (CN); HEFEI XINSHENG OPTOELECTRONICS TECHNOLOGY CO., LTD., Anhui (CN)

(72) Inventors: Yanlin Song, Beijing (CN); Ruifeng Wang, Beijing (CN); Dacheng Deng, Beijing (CN)

(73) Assignees: BOE TECHNOLOGY GROUP CO., LTD., Beijing (CN); HEFEI XINSHENG OPTOELECTRONICS TECHNOLOGY CO., LTD., Anhui (CN)

( * ) Notice: Subject to any disclaimer, the term of this patent is extended or adjusted under 35 U.S.C. 154(b) by 118 days.

(21) Appl. No.: 15/713,509

(22) Filed: Sep. 22, 2017

(65) Prior Publication Data

US 2018/0246022 A1 Aug. 30, 2018

(30) Foreign Application Priority Data

Feb. 28, 2017 (CN) .................... 2017 2 0186925 U

(51) Int. Cl.
*G01N 3/303* (2006.01)
(52) U.S. Cl.
CPC .................... *G01N 3/303* (2013.01)
(58) Field of Classification Search
None
See application file for complete search history.

(56) References Cited

U.S. PATENT DOCUMENTS 6,374,661 B1 * 4/2002 Buratynski ............ G01N 3/30
  73/12.06
6,807,841 B1 * 10/2004 Chen ...................... G01N 3/303
  73/12.06

(Continued)

FOREIGN PATENT DOCUMENTS

CN 104251766 A 12/2014
CN 204154466 U * 2/2015

(Continued)

*Primary Examiner* — Peter J Macchiarolo
*Assistant Examiner* — Jermaine L Jenkins
(74) *Attorney, Agent, or Firm* — McDermott Will & Emery LLP

(57) ABSTRACT

A drop ball test fixture includes a bracket, first stoppers and connecting components. The bracket has bearing surfaces for bearing edges of a panel and to position the panel in a direction parallel to the bearing surfaces. At least part of each of the first stoppers is located above corresponding one of the bearing surfaces. Each connecting component includes a guide rod, a guide groove and a second stopper. The guide groove is formed on corresponding one of the first stoppers. One end of each of the guide rod is connected to the bracket while the other end thereof passes through the guide groove. Connecting structures are provided at different heights of the guide rod, and the second stopper is matched with and connected to corresponding one of the connecting structures at different heights above the guide groove so as to stop the upward movement of the first stopper.

10 Claims, 4 Drawing Sheets

(56) References Cited

U.S. PATENT DOCUMENTS

| | | | | |
|---|---|---|---|---|
| 7,913,539 | B2* | 3/2011 | Su | G01N 3/303 |
| | | | | 73/12.06 |
| 8,453,520 | B2* | 6/2013 | Huang | G01M 99/007 |
| | | | | 73/847 |
| 8,935,952 | B2* | 1/2015 | Dunbar | G01M 1/122 |
| | | | | 703/7 |
| 2013/0213113 | A1* | 8/2013 | Huang | G01M 7/08 |
| | | | | 73/12.13 |
| 2016/0084745 | A1 | 3/2016 | Wang et al. | |

FOREIGN PATENT DOCUMENTS

| | | |
|---|---|---|
| CN | 204535946 U | 8/2015 |
| CN | 104949882 A | 9/2015 |
| CN | 105509984 A | 4/2016 |
| CN | 205192841 U | 4/2016 |

\* cited by examiner

DROP BALL TEST FIXTURE

CROSS-REFERENCE TO RELATED APPLICATION

This application claims priority to Chinese Patent Application No. 201720186925.9, filed on Feb. 8, 2017, titled "DROP BALL TEST FIXTURE", which is incorporated herein by reference in its entirety.

TECHNICAL FIELD

The present disclosure relates to the technical field of fixtures and in particular to a drop ball test fixture.

BACKGROUND

During the production of touch panels, the impact strength of the touch panels is usually detected by a drop ball test fixture.

SUMMARY

Embodiments of the present disclosure provides a drop ball test fixture which can solve the problem of too narrow range of application of the existing drop ball test fixtures caused by their mere applicability to panels of a certain thickness to be tested.

For this purpose, the embodiments of the present disclosure employ the following technical solutions. A drop ball test fixture comprises: a bracket, the bracket having bearing surfaces for bearing edges of a panel to be tested, the bracket being able to position the panel to be tested in a direction parallel to the bearing surfaces; first stoppers, at least part of each of the first stoppers being located above the corresponding bear surface of the bearing surfaces; and connecting components for connecting the first stoppers and the bracket, each of the connecting components comprising a guide rod, a guide groove and a second stopper, the guide groove being formed on a corresponding one of the first stoppers, one end of the guide rod being connected to the bracket while the other end thereof passing through the guide groove, an included angle being formed between the guide rod and the bearing surface, connecting structures being provided at different heights of the guide rod, the second stopper being able to be matched with and connected to corresponding one of the connecting structures at different heights above the guide groove so as to stop the upward movement of corresponding one of the first stoppers.

Further, the bearing surfaces are four bearing surfaces for bearing four edges of the panel to be tested in one-to-one correspondence; and, the first stoppers are four first stoppers, and at least part of each of the four first stoppers is located above corresponding one of the four bearing surfaces.

Further, the first stoppers are barrier strips each of which is arranged in a lengthwise direction of corresponding one of the bearing surfaces and comprises two end regions, and, the two end regions of each of the barrier strips are both connected to the bracket through corresponding one of the connecting components.

Further, the bracket comprises four adjustment levers each comprising a lever body and a slide bushing provided at one end of the lever body, the slide bushing of each of the adjustment levers is slidingly sheathed on the lever body of another adjustment lever of the adjustment levers, and any adjacent two adjustment levers of the adjustment levers are perpendicular to each other; and an elongated positioning slot is provided on an upper surface of the lever body in a lengthwise direction of the lever body, the elongated positioning slot runs through an inner side face of the respective lever body, and the panel to be tested is able to be clamped within a plurality of the elongated positioning slots.

Further, a groove is formed on the upper surface of the lever body, the groove runs through a side face of the elongated positioning slot, and a bottom surface of the groove is higher than a bottom surface of the elongated positioning slot; both corresponding one of the first stoppers and the guide rod are arranged within the groove; and the guide rod are perpendicular to the responding one of the bearing surfaces.

Further, the connecting structures on the guide rod are threads, and the second stopper is a first nut.

Further, a second nut is provided on the guide rod at a position below the guide groovefor stopping the downward movement of corresponding one of the first stoppers.

Further, a bump is provided on a side face of the groove; a cavity is formed within each of the first stopper, and for a specific first stopper of the first stopper, the cavity runs through two side faces of the specific first stopper in a widthwise direction of the specific first stopper; the bump extends into the cavity; the bottom end of the guide rod is connected to the bump; and, in the extension direction of the guide rod, the width of the cavity is greater than the width of the bump.

Further, a slider is provided on an inner surface of the slide bushing; a slide slot is provided on the lever body in a lengthwise direction of the lever body; and, the slider on one adjustment lever is of the fourth adjustment levers are slidingly fitted within the slide slot of another adjustment lever of the fourth adjustment levers.

Further, the slider and the slide bushing are formed integrally.

With regard to the drop ball test fixture provided in the embodiments of the present disclosure, at least part of each of the first stoppers is located above corresponding one of the bearing surfaces to avoid the bounce of the panel to be tested; and, each of the connecting components includes a guide rod, a guide groove and a second stopper, with the guide groove being formed on corresponding one of the first stoppers, one end of the guide rod being connected to the bracket while the other end thereof passing through the guide groove, an included angle being formed between the guide rod and the bearing surface, connecting structures being provided at different heights of the guide rod, and the second stopper being able to be matched and connected to the connecting structures at different heights above the guide groove so as to stop the upward movement of corresponding one of the first stoppers. Therefore, when a thicker panel is to be tested, the second stopper is allowed to be matched and connected to one of the connecting structures at a higher position, so that corresponding one of the first stopper can be adjusted upward. Accordingly, the corresponding one of the first stoppers can avoid the bounce of the thicker panel. In other words, the drop ball test fixture can be applicable to panels of a large thickness. When a panel of a small thickness is to be tested, the second stopper is allowed to be matched with and connected to one of the connecting structures at a lower position, so that the first stopper can be adjusted downward. Accordingly, the corresponding one of first stoppers can avoid the bounce of the thinner panel. In other words, the drop ball test fixture is applicable to panels of a small thickness. That is, with regard to the drop ball test fixture provided in the embodiment of the present disclosure, the height of corresponding one of the first stoppers can be adjusted by adjusting the position at which the second stopper is connected to one of the connecting structures. Accordingly, the drop ball test fixture is applicable to panels of different thicknesses, thus expanding the range of application of the drop ball test fixture.

DETAILED DESCRIPTION

The technical solutions in the embodiments of the present disclosure will be clearly and completely described below with reference to the drawings accompanying the embodiments. Apparently, the embodiments described herein are merely a part but not all of the embodiments of the present disclosure. All other embodiments obtained by a person of ordinary skill in the art without paying any creative effort on the basis of the embodiments in the present disclosure shall fall into the protection scope of the present disclosure.

It is to be noted that, the orientation or ubiety indicated by terms "center", "upper", "lower", "front", "rear", "left", "right", "vertical", "horizontal", "top", "bottom", "inside", "outside" or the like is an orientation or ubiety shown based on the accompanying drawings, and is merely for describing the present disclosure and simplifying the description rather than indicating or implying that the specified device or element must have a particular orientation or be constructed and operated in a particular orientation. Therefore, the terms should not be interpreted as limitations to the present disclosure.

The terms "first" and "second" are merely for illustrative purpose, and should not be interpreted as indicating or implying the relative importance or implicitly indicating the number of the specified technical features. Therefore, the features defined by the terms "first" and "second" can explicitly or implicitly include one or more features. Unless otherwise stated, in the description of the present disclosure, "a plurality of" means two or more.

It is to be noted that, unless otherwise expressly specified and defined, in the description of the present disclosure, the terms "mounting", "joint" and "connection" should be interpreted in a broad sense. For example, the connection may be fixed connection, detachable connection or integral connection; or, may be direct connection or indirect connection by an intermediate member; or, may be internal communication between two elements. A person of ordinary skill in the art may understand the specific meanings of the terms in the present disclosure under specific circumstances.

Figure 1:
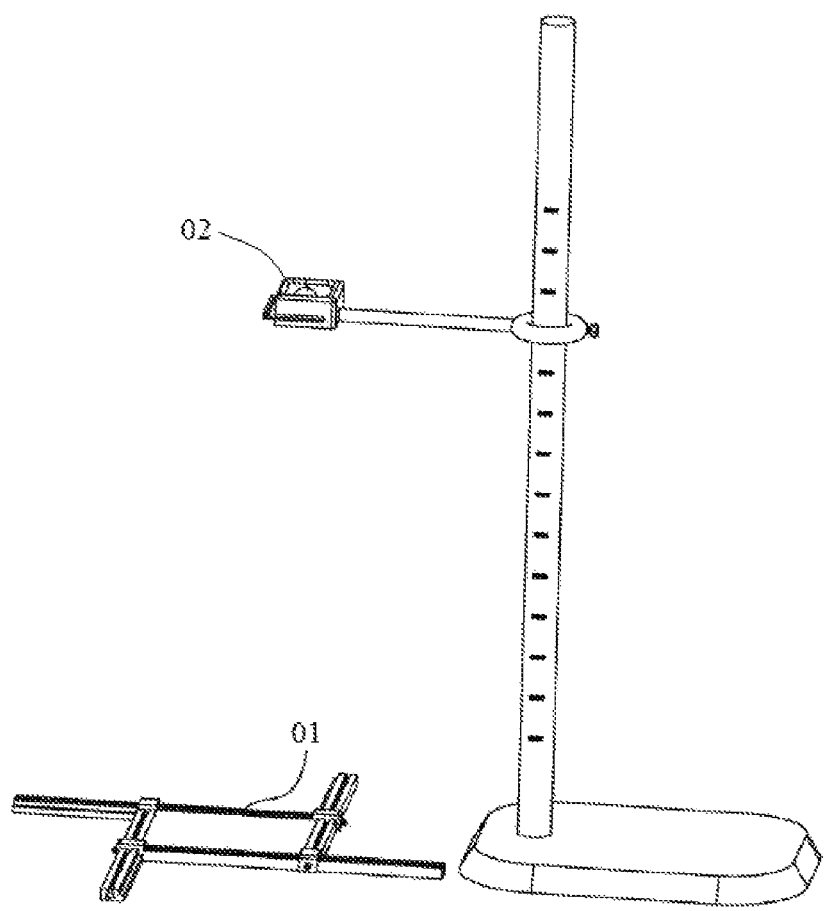
FIG. 1 is a schematic structure diagram of a drop ball test fixture.
Figure 2:
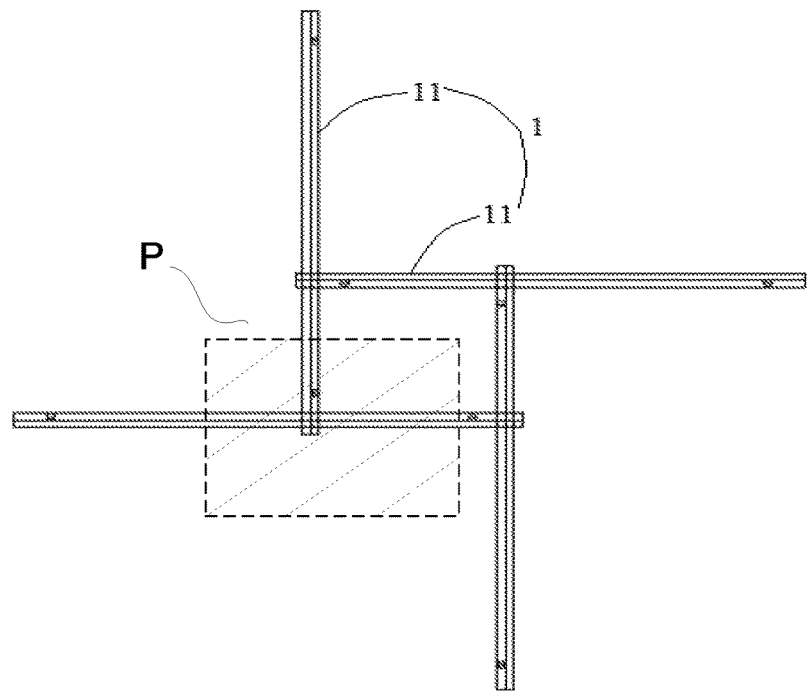
FIG. 2 is a schematic structure diagram of a drop ball test fixture according to the embodiments of the present disclosure.

FIG. 1 shows a drop ball test fixture in the prior art. The drop ball test fixture includes a bracket 01 and a ball-releasing portion 02. The bracket 01 is used for bearing a panel to be tested (not shown). The ball-releasing portion 02 is located above the bracket 01 and used for releasing a ball toward the panel to allow the ball to hit the panel so that the related impact data are obtained for making a judgment. Cover slats (not shown) are provided on the bracket 01, and the cover slats, together with the bracket 01, are used for clamping the panel to prevent the bounce of the panel after the dropping of the ball from influencing the accuracy of the test. However, this drop ball test fixture is merely able to avoid the bounce of panels of a certain thickness and it is not applicable to panels of other thicknesses. The drop ball test fixture has a too narrow range of application.

Referring to FIGS. 2 to 6, the embodiments of the present disclosure provide a drop ball test fixture, including a bracket 1, first stoppers 2 and connecting components 3. The bracket 1 has bearing surfaces A for bearing edges of a panel P to be tested (in order to show bracket 1 clearly, panel P has not yet been supported by bearing surfaces in FIG. 1), and is able to position the panel to be tested in a direction parallel to the bearing surfaces A. At least part of each of the first stoppers 2 is located above corresponding one of the bearing surfaces A. The connecting components 3 are used to connect the first stoppers 2 and the bracket 1. Each of the connecting components 3 includes a guide rod 31, a guide groove 22 and a second stopper 32. The guide groove 22 is formed on the first stopper 2. One end of the guide rod 31 is connected to the bracket 1 while the other end thereof passes through the guide groove 22. An included angle is formed between the guide rod 31 and each of the bearing surfaces A. Connecting structures 311 are provided at different heights of the guide rod 31 and each of the second stoppers 32 is able to be matched with and connected to corresponding one of the connecting structures 311 at different heights above the guide groove 22 so as to stop the upward movement of corresponding one of the first stoppers 2.

With regard to the drop ball test fixture provided in the embodiments of the present disclosure, at least part of each of the first stoppers 2 is located above corresponding one of the bearing surfaces A to avoid the bounce of the panel P to be tested; and, each of the connecting components 3 includes a guide rod 31, a guide groove 22 and a second stopper 32, with the guide groove 22 being formed on corresponding one of the first stoppers 2, one end of the guide rod 31 being connected to the bracket 1 while the other end thereof passing through the guide groove 22, an included angle being formed between the guide rod 31 and corresponding one of the bearing surfaces A, connecting structures 311 being provided at different heights of the guide rod 31, and the second stopper 32 being able to be matched and connected to one of the connecting structures 311 at different heights above the guide groove 22 so as to stop the upward movement of corresponding one of the first stoppers 2. Therefore, when a thicker panel is to be tested, the second stopper 32 is allowed to be matched and connected to one of the connecting structures 311 at a higher position, so that corresponding one of the first stoppers 2 can be adjusted upward. Accordingly, corresponding one of the first stoppers 2 can avoid the bounce of the thicker panel. In other words, the drop ball test fixture can be applicable to panels of a large thickness. When a thinner panel is to be tested, the second stopper 32 is allowed to be matched with and connected to one of the connecting structures 311 at a lower position, so that corresponding one of the first stopper 2 can be adjusted downward. Accordingly, corresponding one of the first stoppers 2 can avoid the bounce of the thinner panel. In other words, the drop ball test fixture is applicable to panels of a small thickness. That is, with regard to the drop ball test fixture provided in the embodiment of the present disclosure, the height of each of the first stoppers 2 can be adjusted by adjusting the positions at which the second stopper 32 is connected to corresponding one of the connecting structures 311. Accordingly, the drop ball test fixture is applicable to panels of different thicknesses, thus expanding the range of application of the drop ball test fixture.

Specifically, there are four bearing surfaces A for bearing four edges of the panel to be tested in one-to-one correspondence; and, there are four first stoppers 2, and at least part of each of first stoppers 2 is located above corresponding one of the bearing surface A in one-to-one correspondence. Hence, four edges of the panel P may be blocked, so that the effect of blocking the panel P to be tested is improved, and the accuracy of the test is thus improved.

Figure 4:
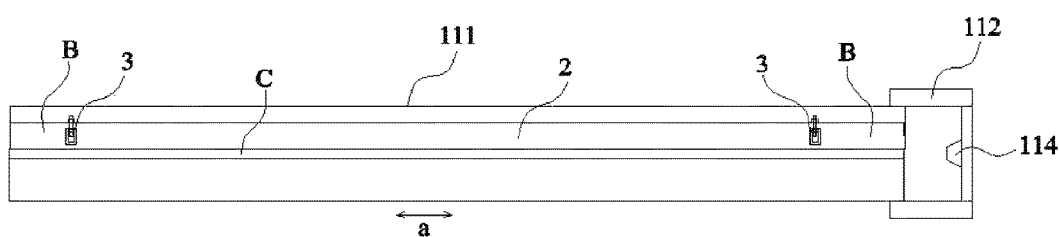
FIG. 4 is a rear view of FIG. 3.

Referring to FIG. 4, the first stoppers 2 are barrier strips each of which are arranged in a lengthwise direction "a" of the corresponding one of the bearing surfaces A. Each of the barrier strips includes two end regions B. And, the two end regions B of each of the barrier strips are both connected to the bracket 1 through the connecting components 3. In other words, each of the barrier strips is connected to the bracket 1 through two connecting components 3. Thus, by adjusting the second stopper 32 in each connecting component 3, the height of the corresponding end region B of the barrier strips may be adjusted. Therefore, an appropriate height is selected according to the shape of the finished product from the client's side for purpose of objective simulation, and the drop ball test fixture can perform effective simulation tests on a panel having a non-uniform thickness on four edges.

To enable the drop ball test fixture to be applicable to rectangular panels of different sizes, referring to FIGS. 2 to 6, in this embodiment, the bracket 1 includes four adjustment levers 11 each including a lever body 111 and a slide bushing 112 provided at one end of the lever body 111. The slide bushing 112 of each of the adjustment levers 11 is slidingly sheathed on the lever body 111 of another one of the adjustment levers 11, and two adjacent adjustment levers 11 of the adjustment levers are perpendicular to each other. An elongated positioning slot C is provided on an upper surface of each of the lever bodies 111 in a lengthwise direction thereof. That is, the elongated positioning slot C is arranged in a horizontal direction. As each of the adjustment levers has the elongated positioning slot C, there are a plurality of elongated positioning slots. The elongated positioning slot C runs through an inner side face of the respective lever body 111, and the panel P to be tested is able to be clamped within a plurality of the elongated positioning slots. Hence, panels of different sizes to be tested can be clamped within a plurality of the elongated position slots by adjusting the distance between two parallel adjustment levers of the adjustment levers 11, so that the drop ball test fixture can be applicable to panels of different sizes to be tested.

Based on the above embodiments, in this embodiment, a groove D is formed on the upper surface of the lever body 111, the groove D runs through a side face of the respective elongated positioning slot C, and a bottom surface of the groove D is higher than a bottom surface of the elongated positioning slot C. Both corresponding one of the first stoppers 2 and the guide rod 31 are arranged within the groove D; and the guide rod 31 is perpendicular to corresponding one of the bearing surface A. In comparison with the case where the guide rod 31 and corresponding one of the bearing surfaces A are inclined, the structure in this embodiment is more regular and has higher stability and reliability in practical applications.

Figure 5:
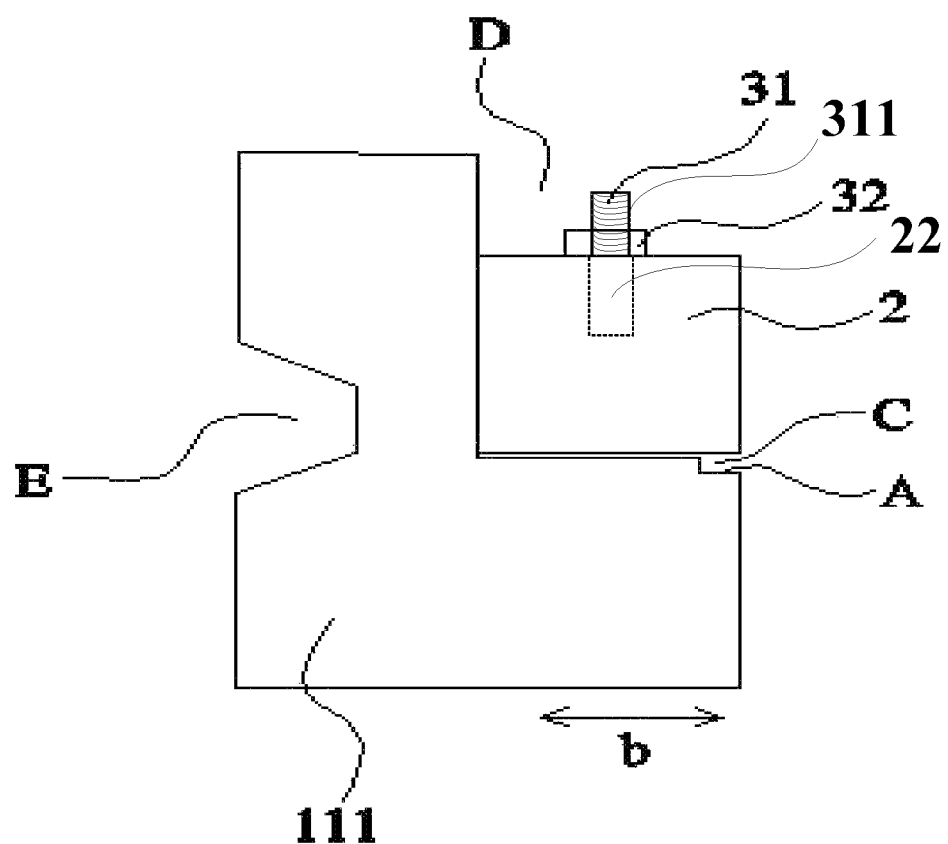
FIG. 5 is a side view of FIG. 3.
Figure 6:
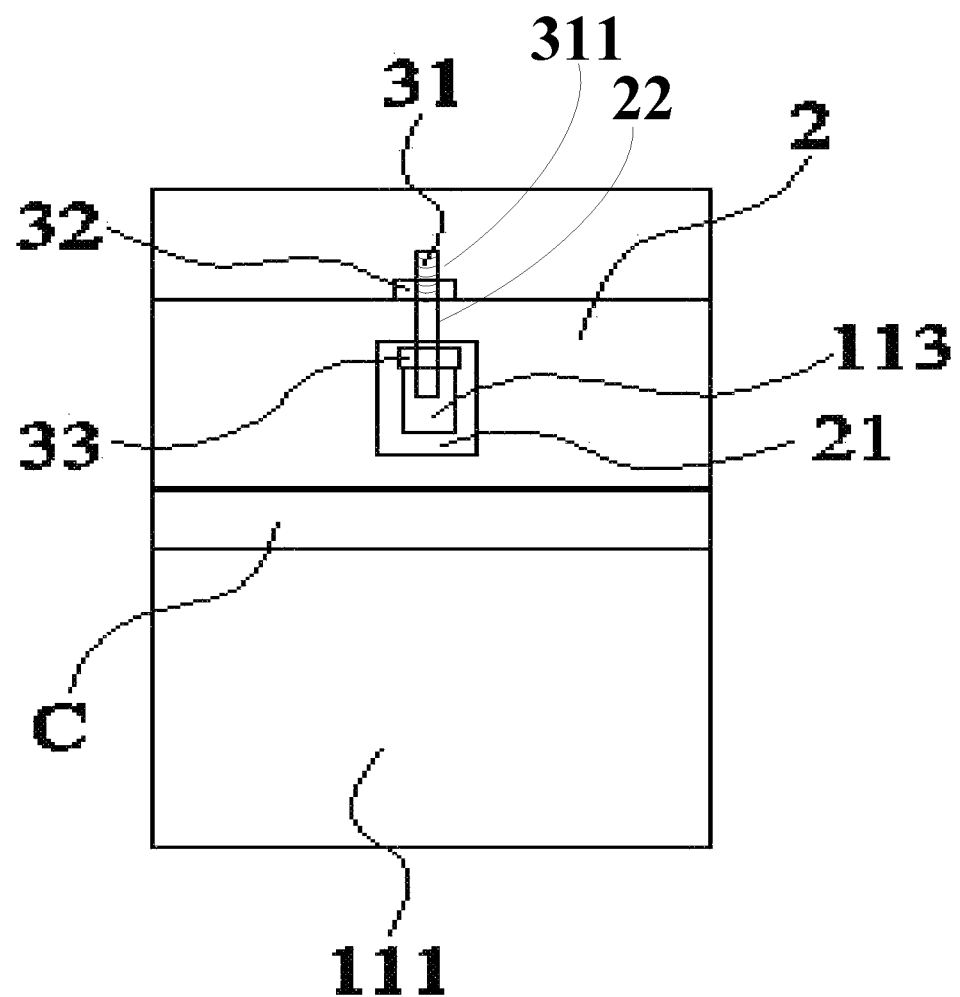
FIG. 6 is a partially enlarged view of FIG. 4.

The connecting structures 311 on the guide rod 31 are realized in various ways. For example, the connecting structures 311 may be a plurality of positioning holes. In this case, the second stopper 32 is a positioning pin, and the positioning pin may be matched and inserted into any one of the positioning holes at different heights above the guide groove 22. For another example, the connecting structures 311 may be threads. In this case, the second stopper 32 is a first nut, and as shown in FIGS. 5 and 6, the first nut may be matched and connected to the threads at different heights above the guide groove. There is inevitably a certain distance between each two adjacent positioning holes, that is, the positioning holes are discontinuous. In contrast, the threads are continuous and allow the height of corresponding one of the first stoppers 2 to be adjusted continuously, so that the drop ball test fixture can be applicable to panels of various thicknesses, thus further expanding the range of application of the drop ball test fixture. Therefore, in this embodiment, preferably, the connecting structures 311 on the guide rods 31 are threads, and the second stopper 32 is a first nut.

For the purpose of labor-saving, in this embodiment, a second nut 33 is provided on the guide rod 31 at a position below the guide groove 22, and the second nut 33 is able to stop the downward movement of corresponding one of the first stoppers 2. Hence, no person is required to lift up corresponding one of the first stopper 2 when placing or taking out the panel P. Thus, the purpose of labor-saving is realized.

Referring to FIGS. 5 and 6, a bump 113 is provided on side face of the groove D and a cavity 21 is formed within each of the first stoppers 2. The cavity 21 runs through two side faces of corresponding one of the first stoppers 2 in a widthwise direction "b" of the first stopper 2. The bump 113 extends into the cavity 21. The bottom end of the guide rod 31 is connected to the bump 113. In the extension direction of the guide rod 31, the width of the cavity 21 is greater than the width of the bump 113 in order to prevent the bump 113 from influencing the movement of the first stopper 2 in the extension direction of the guide rod 31. In this case, the guide groove 22 is located above the cavities 21, and the second nut 33 is located within the cavity 21, thus avoiding placing the second nut 33 below corresponding one of the first stoppers 2 so that too large a distance between corresponding one of the first stoppers 2 and corresponding one of the bearing surfaces A when t. The drop ball test fixture can thus be applicable to panels of a small thickness to be tested.

Figure 3:
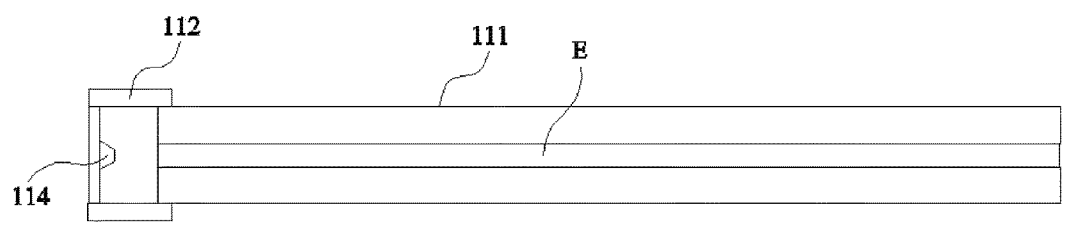
FIG. 3 is a schematic diagram of adjustment levers in the drop ball test fixture according to the embodiments of the present disclosure.

In order to increase the stability and reliability of the drop ball test fixture, referring to FIGS. 3 to 5, in this embodiment, a slider 114 is provided on an inner surface of the slide bushing 112. A slide slot E is provided on the lever body 111 in a lengthwise direction of the lever body. The slider 114 on one adjustment lever of the adjustment levers 11 is slidingly fitted within the slide slot E of another adjustment lever of the adjustment levers 11. Hence, the contact area between the sliding bushing 112 and the level body 111 is increased, and the friction is thus increased. Thus, the fixture is less likely to deform under the vibration generated when the ball hits the panel P. That is, the distance between two parallel adjustment levers of the adjustment levers 11 is less likely to become larger, thus improving the stability and reliability of the drop ball test fixture. The drop ball test fixture of the present disclosure can be used with existing vehicle terms to objectively simulate practical situations.

Preferably, the slider 114 and the slide bushing 112 are formed integrally. Hence, no additional connecting structures 311 will be used to connect the slider 114 with the sliding bushing 112, so that the structure of the fixture is simplified and the cost is saved.

Both the adjustment lever 11 and the first stopper 2 are preferably made of bakelite. Since the bakelite is high in strength and less deformable, when in use, the fixture may be kept in an available state for a long period of time.

All the guide rods 31, the first nuts and the second nuts 33 are made of stainless steel in order to prevent sweat on hands from corroding them.

The foregoing descriptions merely show specific implementations of the present disclosure, but the protection scope of the present disclosure is not limited thereto. Any person of skill in the art may easily conceive of variations or replacements within the technical scope disclosed by the present disclosure, and these variations or replacements shall fall into the protection scope of the present disclosure. Therefore, the protection scope of the present disclosure shall be subject to the protection scope of the claims.

What is claimed is:

1. A drop ball test fixture, comprising:
   a bracket, the bracket having bearing surfaces for bearing edges of a panel to be tested, the bracket being able to position the panel to be tested in a direction parallel to the bearing surfaces;
   first stoppers, at least part of each of the first stoppers being located above the corresponding bear surface of the bearing surfaces; and
   connecting components for connecting the first stoppers and the bracket, each of the connecting components comprising a guide rod, a guide groove and a second stopper, the guide groove being formed on a corresponding one of the first stoppers, one end of the guide rod being connected to the bracket while the other end thereof passing through the guide groove, an included angle being formed between the guide rod and the bearing surface, connecting structures being provided at different heights of the guide rod, the second stopper being able to be matched with and connected to corresponding one of the connecting structures at different heights above the guide groove so as to stop the upward movement of corresponding one of the first stoppers.

2. The drop ball test fixture according to claim 1, wherein the bearing surfaces are four bearing surfaces for bearing four edges of the panel to be tested in one-to-one correspondence; and, the first stoppers are four first stoppers, and at least part of each of the four first stoppers is located above corresponding one of the four bearing surfaces.

3. The drop ball test fixture according to claim 2, wherein the first stoppers are barrier strips each of which is arranged in a lengthwise direction of corresponding one of the bearing surfaces and comprises two end regions, and, the two end regions of each of the barrier strips are both connected to the bracket through corresponding one of the connecting components.

4. The drop ball test fixture according to claim 1, wherein the bracket comprises four adjustment levers each comprising a lever body and a slide bushing provided at one end of the lever body, the slide bushing of each of the adjustment levers is slidingly sheathed on the lever body of another adjustment lever of the adjustment levers, and any adjacent two adjustment levers of the adjustment levers are perpendicular to each other; and
   an elongated positioning slot is provided on an upper surface of the lever body in a lengthwise direction of the lever body, the elongated positioning slot runs through an inner side face of the respective lever body, and the panel to be tested is able to be clamped within a plurality of the elongated positioning slots.

5. The drop ball test fixture according to claim 4, wherein a groove is formed on the upper surface of the lever body, the groove runs through a side face of the elongated positioning slot, and a bottom surface of the groove is higher than a bottom surface of the elongated positioning slot; both corresponding one of the first stoppers and the guide rod are arranged within the groove; and the guide rod are perpendicular to the responding one of the bearing surfaces.

6. The drop ball test fixture according to claim 5, wherein the connecting structures on the guide rod are threads, and the second stopper is a first nut.

7. The drop ball test fixture according to claim 6, wherein a second nut is provided on the guide rod at a position below the guide groovefor stopping the downward movement of corresponding one of the first stoppers.

8. The drop ball test fixture according to claim 7, wherein a bump is provided on a side face of the groove; a cavity is formed within each of the first stopper, and for a specific first stopper of the first stopper, the cavity runs through two side faces of the specific first stopper in a widthwise direction of the specific first stopper; the bump extends into the cavity; the bottom end of the guide rod is connected to the bump; and, in the extension direction of the guide rods, the width of the cavity is greater than the width of the bump.

9. The drop ball test fixture according to claim 4, wherein a slider is provided on an inner surface of the slide bushing; a slide slot is provided on the lever body in a lengthwise direction of the lever body; and, the slider on one adjustment lever is of the fourth adjustment levers are slidingly fitted within the slide slot of another adjustment lever of the fourth adjustment levers.

10. The drop ball test fixture according to claim 9, wherein the slider and the slide bushing are formed integrally.

* * * * *